United States Patent [19]
Yamazaki et al.

[11] Patent Number: 6,149,796
[45] Date of Patent: Nov. 21, 2000

[54] METHOD OF MANUFACTURING HYDROXYAPATITE AND AQUEOUS SOLUTION OF BIOCOMPOUNDS AT THE SAME TIME

[75] Inventors: Hiraku Yamazaki; Atsushi Yamazaki; Yoshiko Yamazaki; Yutaka Yamazaki, all of Chiba, Japan

[73] Assignee: Hiraki Yamazaki, Chiba, Japan

[21] Appl. No.: 09/295,987

[22] Filed: Apr. 21, 1999

[30] Foreign Application Priority Data

Jul. 8, 1998 [JP] Japan .................................. 10-192914

[51] Int. Cl.$^7$ ..................................................... A61K 35/12
[52] U.S. Cl. ......................... 205/490; 205/701; 205/766; 205/770
[58] Field of Search .................................. 205/490, 701, 205/766, 770

[56] References Cited

U.S. PATENT DOCUMENTS 2,355,231   8/1944   Moore ..................................... 205/701

*Primary Examiner*—Arun S. Phasge
*Attorney, Agent, or Firm*—Christensen O'Connor Jophnson Kindness PLLC

[57] ABSTRACT

A method of manufacturing an aqueous solution of biocompounds containing peptide as a major component and a hydroxyapatite containing minerals and being useful an inorganic or organic composite material from tissue in an electrolytic cell by performing the electrolysis of an aqueous solution of the tissue and by taking advantage of an electrode reaction using suitable electrodes. In this case, a DC current is passed between the electrodes in the aqueous solution, thereby dissolving and crystallizing the tissue components. After unreacted matters are removed, the resultant mixed solution is separated into solid matters and a liquid. The aqueous solution of biocompounds is obtained from the filtrate, and the hydroxyapatite is obtained from the recrystallized solid matters.

8 Claims, 2 Drawing Sheets

METHOD OF MANUFACTURING HYDROXYAPATITE AND AQUEOUS SOLUTION OF BIOCOMPOUNDS AT THE SAME TIME

BACKGROUND OF THE INVENTION

This invention relates to a method of manufacturing a hydroxyapatite and an aqueous solution of biocompounds at the same time from tissue (vital tissue) by taking advantage of an electrochemical reaction. Hydroxyapatite is useful as toothpaste, biomaterials, cosmetics, etc., while an aqueous solution of tissue is useful as a natural medium.

Tissue is biologically synthesized by a living body by making use of bioelements. The tissue is formed of biodegradable materials which may be utilized as a nutrition for the species of other kind.

Specifically, this invention is related to a method wherein the biomaterials are to be obtained through the decomposition and separation of tissue by employing an electrochemical reaction in an aqueous solution instead of employing biodegradation, thereby making it possible to mass-produce various kinds of biomelecules concurrently and more cheaply as compared with the biodegradation.

This invention is further related to a method wherein tissue is separated as a biochemical raw material by a process similar to the carbonization of coal or petroleum refining where chemical raw materials are separated from natural resources. More specifically, this invention related to a method of dissolving and recrystallizing tissue by making use of an electrochemical reaction, thereby transforming the tissue into biochemical raw materials.

In particular, this invention related to a method wherein an aqueous solution of biocompounds and hydroxyapatite are to be simultaneously produced from tissue containing minerals, lipid, saccharides, protein, collagen, amino acid, nucleoside and hydroxyapatite.

More particularly, this invention related to a method of dissolving and recrystallizing biomaterials in an aqueous solution by making use of an electrode reaction in the aqueous solution without necessitating the employment of chemicals, thereby making it possible to simultaneously obtain, in large quantity, safely and cheaply, not only an aqueous solution of biocompounds including a small quantity of minerals, amino acid, nucleoside, collagen, lipid, saccharides and protein; but also hydroxyapatite containing minerals, protein, lipid, saccharides, collagen, amino acid and nucleoside.

Since peptide and hydroxyapatite can be incorporated in a tissue and are indispensable materials for the growth the tissue, the natural raw materials of them or the synthesized materials of them have been conventionally employed as a culture medium, as an artificial bone, as a raw material of bioceramics, etc.

According to the conventional method of transforming a waste tissue (a raw material) into useful resources such as peptide and hydroxyapatite, the waste tissue as a raw material has been subjected to treatments such as dissolution, extraction, baking, etc. in a specific manner depending on the kinds of compounds contained in the waste tissue, thereby transforming the waste tissue into useful resources.

For instance, peptide has been manufactured in such manners that a natural raw material (for example, protein) is decomposed using chemicals (such as HCl) into peptide, or a natural or synthesized raw material is subjected to a biotechnology using enzyme, whereby synthesizing peptide.

In the case of producing peptide by decomposing a natural raw material by making use of chemicals however, the decomposition reaction involved therein can be hardly controlled, thereby giving low yields of peptide even though a relatively large amount of peptide can be obtained within a short period of time.

On the other hand, in the case of synthesizing peptide by means of biotechnology, a minute controlling of enzyme reaction is required, thereby making it difficult to obtain various kinds of peptide in large quantity and cheaply.

In the meantime, hydroxyapatite is now noticed as a tissue affinity material. This hydroxyapatite has been conventionally manufactured mainly by means of wet chemical synthesis. There have been proposed various wet processes for manufacturing the hydroxyapatite. For example, Japanese Patent Unexamined Publication H4-20971 teaches a method of synthesizing hydroxyapatite by dropping, with stirring, an aqueous phosphate solution into a slurry of calcium hydroxide in an inert gas atmosphere, wherein a biochemical buffer solution such as Tris buffer solution or Good's buffer solution is employed thereby to obtain a hydroxyapatite having a Ca/P ratio of 1.67 in theoretical composition ratio.

The hydroxyapatite chemically synthesized in this manner is however accompanied with a defect that it scarcely contains a small quantity of minerals which are inherently contained in the tissue, so that this chemically synthesized hydroxyapatite is not expected to be readily and effectively utilized by a living body. Therefore, when this chemically synthesized hydroxyapatite is employed for a medical purpose, e.g. as a filling material for a defective portion of bone, a problem of insufficient compatibility of the hydroxyapatite with the living body will be raised. Moreover, since a strict pH control is required in the chemical synthesis of the hydroxyapatite, it is difficult to mass-produce the hydroxyapatite, thus leading to an increase in manufacturing cost thereof.

More recently, there has been developed a technique to produce natural hydroxyapatite from the bone of pig or cattle in place of the aforementioned chemical synthesis means.

Namely, according to this recent technique, the bone of pig or cattle is caused to fluidize while being baked at a high temperature in a furnace, and then a gaseous water is sprayed onto the fluidized bone so as to remove the protein or fat that have been adhered to the fluidized bone. However, since the bone is baked at a high temperature in this method, the degree of crystallinity of the hydroxyapatite constituting the main component of the bone is caused to change, thereby deteriorating the absorbability of the hydroxyapatite to human body.

A method which is capable of overcoming the aforementioned problem has been also proposed (Japanese Patent Unexamined Publication H2-188415). According to this method, the bone charcoal or baked bone that has been derived from animal products is dissolved in an inorganic acid and then subjected to a fine filtration, the resultant filtrate being subsequently added with an alkali thereby to precipitate hydroxyapatite.

However, since the hydroxyapatite to be obtained by the aforementioned technique is produced by dissolving baked bone for instance using an acid and then precipitated using an alkali, the resultant hydroxyapatite is in defect of organic compounds such as protein, amino acid, peptide, etc. even though it contains minerals. As a result, this resultant hydroxyapatite is accompanied with the problems that it is poor in compatibility with human body as well as in absorbability to human body.

When these conventional hydroxyapatites are employed as a tooth-paste, the abrasive action thereof is too great so that it will cause a prominent gingival recession or abrasion of enamel of tooth, so that only a little quantity of these conventional hydroxyapatites could be employed as an abrasive in the tooth-paste. Further, since some of these conventional hydroxyapatites contain no mineral, the effect of the enzyme existing in saliva and having a capability of forming tooth to absorb the hydroxyapatite and to remedy the defective portion of enamel of tooth becomes very small.

BRIEF SUMMARY OF THE INVENTION

According to a first aspect of the present invention, there is provided a method of manufacturing a hydroxyapatite and an aqueous solution of biocompounds at the same time from tissue by taking advantage of an electrode reaction, which comprises the steps of:

dissolving a tissue filled in an anode vessel of an electrolytic apparatus by passing an electric current through said tissue, said electrolytic apparatus comprising;
an electrolytic bath filled with an electrolyte;
a cathode vertically disposed in said electrolyte;
said anode vessel provided on an outer wall thereof with a large number of small holes for allowing said electrolyte to flow therethrough and entirely immersed in said electrolyte; and
an anode vertically disposed in said anode vessel;
allowing part of said tissue dissolved by said electric current to crystallize in an aqueous cathode solution in the vicinity of said cathode;
filtering said electrolyte to obtain a filtrate and a residue;
obtaining said aqueous solution of biocompounds from said filtrate; and
obtaining said hydroxyapatite from said residue.

According to a second aspect of the present invention, there is also provided a method of manufacturing an aqueous solution of biocompounds from tissue by dissolving tissue, which comprises the steps of:

dissolving a tissue consisting a mixture comprising one or more kinds selected from meat, skin, lipid, blood and organs and filled in an anode vessel of an electrolytic apparatus by passing an electric current through said tissue, said electrolytic apparatus comprising;
an electrolytic bath filled with an electrolyte;
a cathode vertically disposed in said electrolyte;
said anode vessel provided on an outer wall thereof with a large number of small holes for allowing said electrolyte to flow therethrough and entirely immersed in said electrolyte; and
an anode vertically disposed in said anode vessel;
filtering said electrolyte to obtain a filtrate; and
obtaining said aqueous solution of biocompounds from said filtrate.

Other features of the present invention will be more clearly understood from the following description.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

According to the present invention, the electrode reaction system is controlled by suitably selecting the conditions of electrolysis such as the kind of composition of tissue; the kind, composition, concentration and temperature of supporting electrolyte; the anode current density; and the material and shape of anode; the electric potential; and the structure of cell, thereby making it possible to obtain an aimed peptide with high yield. As a result, it is possible to obtain, at low cost and in large quantity, the nutrient compounds for bacteria that can be employed for a saprophytic infection-free incubation of bacteria.

Figure 1:
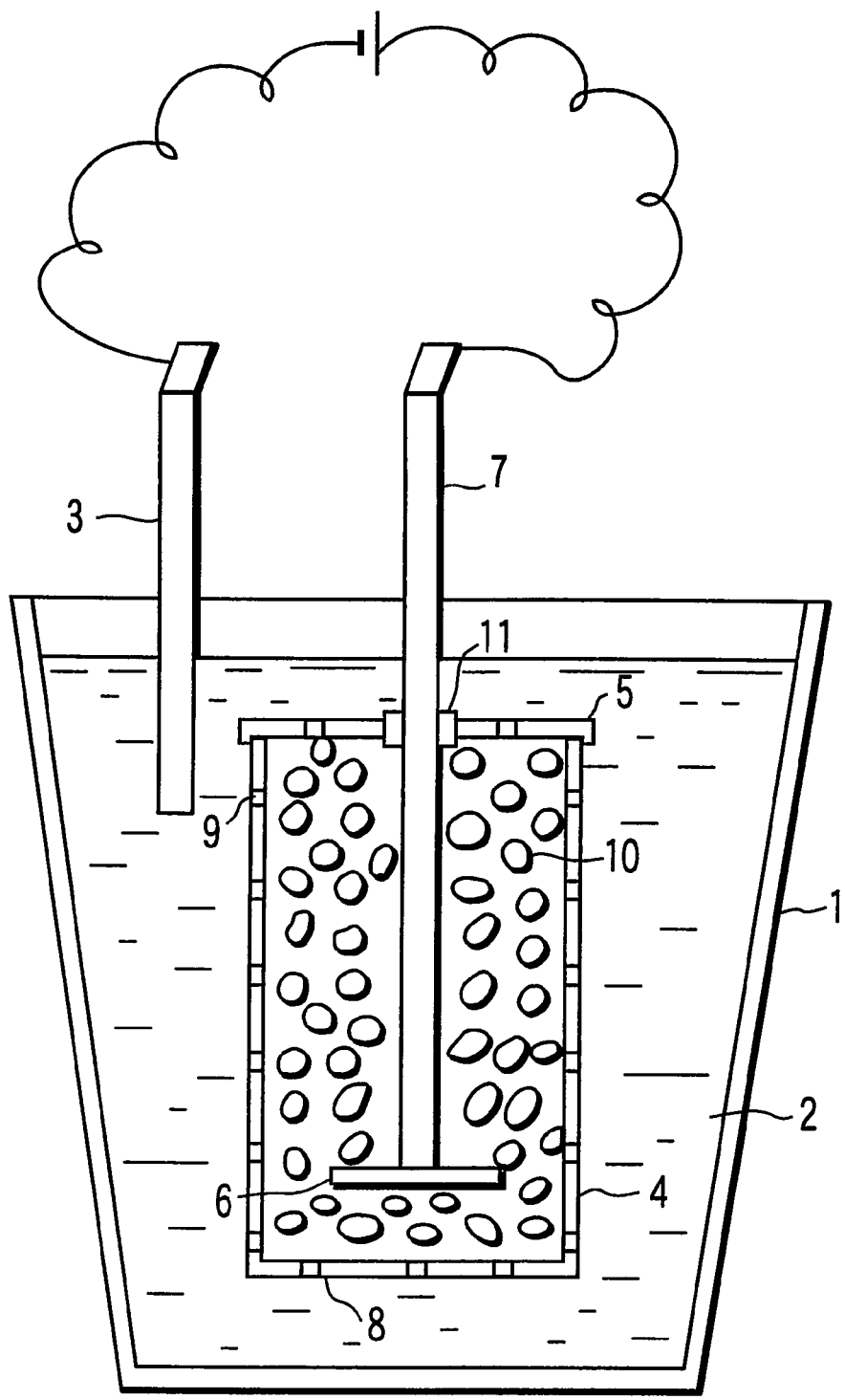
FIG. 1 is a cross-sectional view schematically illustrating an apparatus to be employed in one example of the present invention.

FIG. 1 shows a cross-sectional view of an apparatus to be employed in the method for manufacturing peptide and hydroxyapatite according to one example of invention. Referring to FIG. 1, an electrolyte solution 2 is filled in an electrolytic cell 1. As for the supporting electrolyte, various kinds of electrolyte such as physiological saline, sea water, brine, an edible organic acid such as vinegar, etc. can be preferably employed. In this electrolyte solution 2, there is vertically erected a cathode 3 so as to be contacted with the electrolyte solution 2.

An anode vessel 4 provided with a cap 5 is disposed at the central portion of this electrolytic cell 1. An anode 6 is horizontally disposed in this anode vessel 4.

This anode 6 is supported at the central portion thereof by an electrode-supporting member 7. Namely, the lower portion of the electrode-supporting member 7 is fixed to the central portion of the anode 6, while the upper of the electrode-supporting member 7 is protruded out of the electrolytic cell 1. This electrode-supporting member 7 is formed of a graphite rod whose surface is covered by an insulating film such as a polyethylene film.

By the way, both cathode 3 and anode 6 are made of graphite. Depending on the end-use, Pt or DSA (Dimensionally Stable Anode) may be employed as the anode 6.

The anode vessel 4 is provided on the side walls and bottom plate thereof with a large number of small holes 8 and 9.

This apparatus can be used as follows. Namely, first of all, a large number of pieces of tissue (a mixture of tissues) is charged as a raw material into the anode vessel 4. As this raw material, the waste of animal product such as the bone, tooth, skin, meat of pig, cattle, etc. can be employed by crushing them into a suitable size weighing about 0.3 g to 30 g.

The anode vessel 4 is held immersed in the electrolyte solution 2 (a cathode solution) of the electrolytic cell 1. Usually, the anode vessel 4 is selected to have a height which is smaller than the level of the electrolyte filled in the electrolytic cell 1, so that when the anode vessel 4 filled with a mixture of tissue 10 as a raw material is immersed in the electrolyte solution 2, the anode vessel 4 can be easily and entirely covered by the electrolyte 2 and held therein.

Although the top portion of the electrode-supporting member 7 is protruded out of the upper portion of the anode vessel 4, a packing 11 is applied to the electrode-supporting member-pierced portion of the cap 5 of the anode vessel 4 thereby preventing the gas to be generated from the anode from being concentrically leaked out through this pierced portion.

Under this condition, usually a DC current of 10 V is impressed between the electrodes and an electric current of 10 A is passed therebetween for a predetermined period of time. As a result, the tissue 10 charged in the anode vessel 4 is allowed to decompose and hence, the color of the electrolyte is gradually turned into brown color due to the cathode 3, and at the same time, a large number of fine particles begin to float in the electrolyte.

When the passage of electric current is further continued for 160 hours for instance under this condition, the fine particles that have been floated begin to settle at the bottom of the electrolytic cell 1. When the fine particles have been settled at the bottom of the electrolytic cell 1, the passage of electric current is suspended, and the electrolyte solution 2 is taken out of the electrolytic cell 1 by making use of a pump.

The electrolyte 2 thus taken out is then allowed to stand, and then, unreacted tissues that have gone down immediately and a little amount of lipid floating on the surface of electrolyte are removed. Thereafter, the electrolyte 2 containing the fine particles is filtered to obtain an aqueous solution of biocompounds containing peptide as a major component as well as the fine particles containing hydroxyapatite as a major component.

Namely, this aqueous solution of biocompounds is obtained from the filtrate. By the way, if this aqueous solution of biocompounds is to be employed as a medium, it may be convenient to employ physiological saline as an electrolyte solution, thereby making it possible to employ this obtained aqueous solution of biocompounds as it is as an incubation medium containing nutrient compounds for bacteria.

The residue constituted by the fine particles containing hydroxyapatite as a major component is further processed wherein water is added to the residue and, after stirring and standing, the resultant supernatant is removed. This process is usually repeated about 10 times so as to remove amino acid, collagen, protein, lipid, saccharides and nucleoside that have been excessively adhered on the surface of the fine particles as well as to remove the supporting electrolyte. Thereafter, the resultant solution is filtered using a filter cloth thereby to recover a paste-like residue, which is then allowed to dry for one week or more to obtain a fine particulate hydroxyapatite.

If an aqueous solution of biocompounds of high concentration is desired to be obtained, the filtrate containing peptide is repeatedly subjected to an electrolysis in the same manner as explained above until an aqueous solution of biocompounds of desired concentration is obtained.

Specifically, the manufacture of an aqueous solution of biocompounds and hydroxyapatite was performed using a tissue as a raw material in an apparatus of the same construction as shown in FIG. 1. Namely, an electrolytic cell 1 having a capacity of 25 L and being made of polypropylene was employed. The anode vessel employed herein was also made of polypropylene and had a capacity of 9 L.

The tissue employed as a raw material was formed of 5 kg of pig bone crushed into pieces having a size of about 5 to 50 mm (square) and 1 kg of the muscle of cattle. As for the electrolyte solution, a 10% aqueous solution of brine was employed. Under this condition, a DC current of 10 V was impressed to pass an electric current of 10 A between the electrodes for 160 hours. After the electrolysis using this magnitude of electric current was finished, the resultant electrolyte was transferred using a pump to a separate vessel.

Then, fine muscle and lipid floating on the surface of this electrolyte as well as the unreacted bone settled on the bottom of the electrolytic cell 1 were removed. Subsequently, the resultant electrolyte was filtered to separately obtain an aqueous solution of biocompounds containing peptide as a major component and fine particles containing hydroxyapatite.

Thereafter, the filtrate was again charged as a raw material into the electrolytic cell 1. After supplementary supporting electrolyte and water were added to the filtrate in the electrolytic cell 1, the passage of electric current was continued under the same condition.

After the aforementioned procedures including the electrolysis and filtration were repeated four times thereby performing the electrolysis of 640 hours in total, all of the electrolyte was taken up from the electrolytic cell 1 using a pump and then filtered thereby to obtain 20 L of an aqueous solution of peptide having a concentration of about 5%.

After the electrolysis apparatus was replenished with an additional electrolyte solution, and the anode vessel was also replenished with a suitable quantity of tissue to supplement the decrease of the previous tissue, the aforementioned procedures were again repeated. This operation was intermittently continued for about 6 months (4,160 hours).

On the other hand, the fine particles and suspended matters in the electrolyte solution were taken out through filtration. This residual matters were then added with 20 L of water and, after being stirred, allowed to stand for 2 hours or more, after which 10 L of the supernatant was removed. After repeating this operation 10 times, the resultant mixed solution was filtered using a filter cloth to obtain a residue which was then allowed to air-dry for one week or more thereby to obtain a bulky or granular hydroxyapatite.

When 129 g of this hydroxyapatite was heat-treated for one hour at temperatures of 100° C., 300° C. and 700° C., the weight of the hydroxyapatite was reduced to 120 g, 99 g and 91 g, respectively. Further, when each heat-treated hydroxyapatite was again left in the external atmosphere for 5 hours, the weight of each hydroxyapatite was increased by about 4 g due to the moisture absorption by each hydroxyapatite.

The heating loss of the hydroxyapatite was found different depending on the manufacturing condition, and the ratio of loss after the heat treatment at 100° C., 300° C. and 700° C. in subsequent to the air-drying were found as follows. Namely, the ratio of loss of the hydroxyapatite when it was heated at 100° C. after the air-drying was found 4 to 8%. When this heat-treated hydroxyapatite was further heated at 100° C. to 300° C., the ratio of loss of the hydroxyapatite was found 11 to 20%. Further, when this heat-treated hydroxyapatite was further heated at 300° C. to 700° C., the ratio of loss of the hydroxyapatite was found 4 to 9%.

Figure 2:
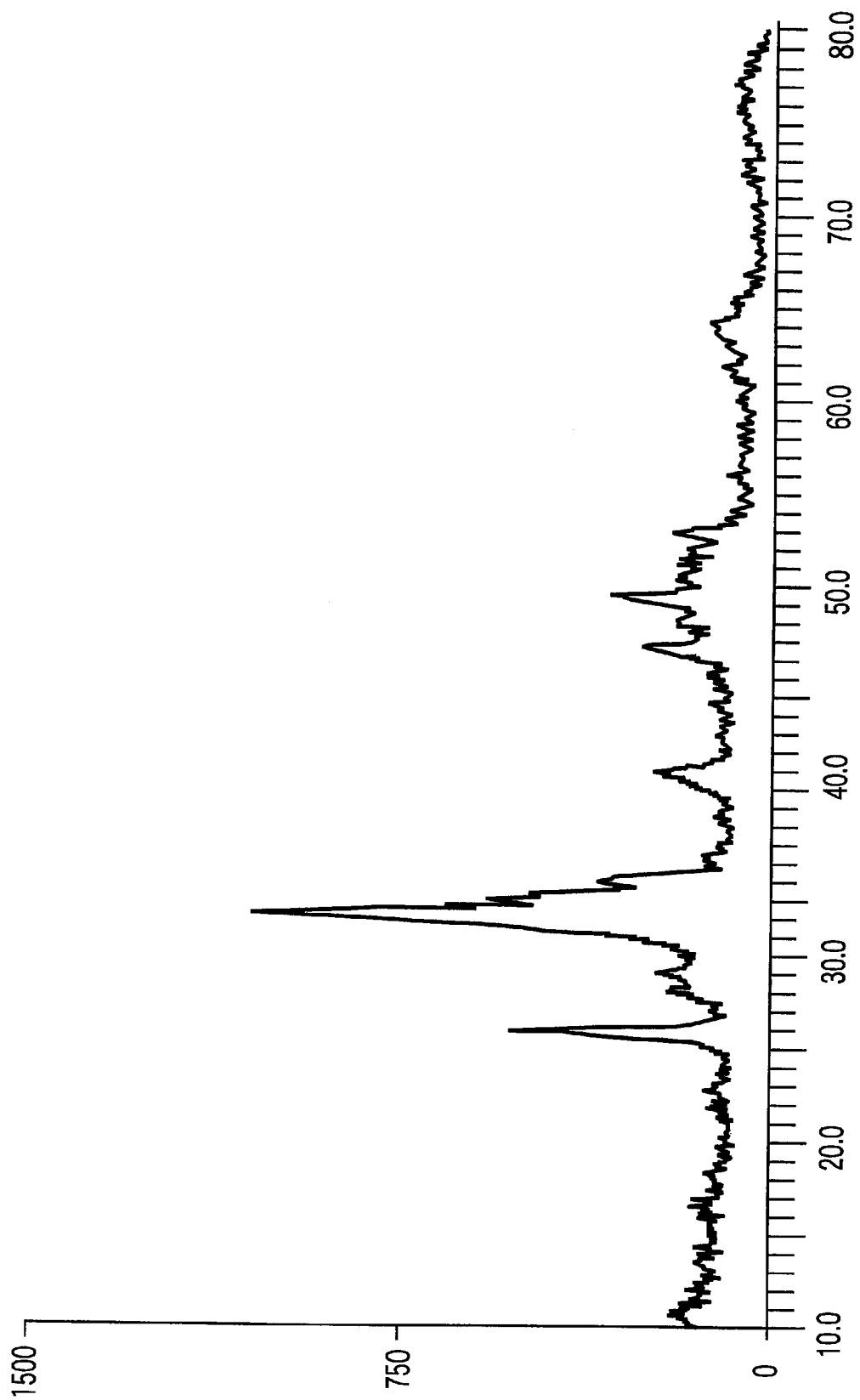
FIG. 2 is an X-ray chart of a hydroxyapatite obtained according to the present invention.

The yield of the hydroxyapatite obtained according to the aforementioned operation was found 0.5 to 1.5 kg/160 hours. When this hydroxyapatite was examined by means of X-ray diffraction, the results shown in Table 1 were obtained. These results were also shown in FIG. 2. As seen from these results, the peak intensity of the hydroxyapatite thus produced was found quite identical with the known peak intensity of pig.

TABLE 1

| Measurement value | | | Ca₅(PO₄)₃(OH) (Hydroxylapatite) | |
|---|---|---|---|---|
| Angle 2θ | Lattice spacing d(Å) | Strength (1/1o) | Distance of space d(Å) | Strength (1/1o) |
| | | | (8.17 | 12) |
| | | | (5.26 | 6) |
| | | | (4.72 | 4) |
| | | | (4.07 | 10) |
| 22.84 | 3.890 | 19 | 3.88 | 10 |
| | | | (3.51 | 2) |
| 25.88 | 3.440 | 42 | 3.44 | 40 |
| 28.20 | 3.162 | 20 | 3.17 | 12 |
| 28.88 | 3.089 | 25 | 3.08 | 18 |
| 32.00 | 2.794 | 100 | 2.814 | 100 |
| | | | 2.778 | 60 |
| | | | 2.720 | 60 |
| | | | 2.631 | 25 |
| | | | (2.528 | 6) |
| | | | (2.296 | 8) |
| 39.72 | 2.267 | 25 | 2.262 | 20 |
| | | | (2.228 | 2) |
| | | | (2.148 | 10) |
| | | | (2.134 | 4) |
| 43.92 | 2.060 | 8 | 2.065 | 8 |
| | | | (2.040 | 2) |
| | | | (2.000 | 6) |
| 46.68 | 1.944 | 27 | 1.943 | 30 |
| 47.88 | 1.898 | 21 | 1.890 | 16 |
| | | | (1.871 | 6) |
| 49.56 | 1.838 | 26 | 1.841 | 40 |
| 50.56 | 1.804 | 18 | 1.806 | 20 |
| 51.40 | 1.776 | 18 | 1.780 | 12 |
| 52.16 | 1.752 | 18 | 1.754 | 16 |
| 53.24 | 1.719 | 17 | 1.722 | 20 |
| | | | (1.684 | 4) |
| | | | (1.644 | 10) |
| | | | (1.611 | 8) |
| | | | (1.587 | 4) |
| | | | (1.542 | 6) |

As seen from the above explanation, it is now possible according to the present invention to simultaneously obtain an aqueous solution of biocompounds containing coagulation-free peptide as a major component and a recrystallized hydroxyapatite which is similar to the natural hydroxyapatite such as that of the bone and tooth of animal containing minerals, protein and amino acid. Moreover, according to the present invention, it is possible to obtain these materials quite easily and safely, requiring only a small quantity of electricity without necessitating the employment of chemicals.

This aqueous solution of biocompounds containing peptide as a major component can be employed as an alternate medium for the conventional bacterial medium comprising tryptone, etc. Furthermore, although the conventional bacterial medium is accompanied with a problem of saprophytic infection, this problem can be overcome by the present invention, and hence a mass incubation of bacteria can be realized at low cost.

Since raw materials are not to be baked as in the case of the conventional manufacturing method of natural hydroxyapatite, the hydroxyapatite to be obtained by the method of the present invention is relatively rich in water content, protein and amino acid, so that it is excellent in compatibility and absorbability in relative with human body.

Therefore, a hydroxyapatite powder or paste of the present invention can be employed as it is, i.e. without an additive, for the manufacture of a tooth-paste or a face cleanser (pack), etc. Further, it has been confirmed that when this hydroxyapatite powder or paste is employed as it is as a tooth-paste, the nicotine of cigarette or the dental plaque that has been adhered on the surface of enamel or cement of tooth can be easily removed.

Additionally, when this hydroxyapatite powder or paste is employed as a face cleanser (pack), the lipid adhered on the surface of face or of hands and feet can be very effectively absorbed by this hydroxyapatite powder or paste, and at the same time, the blood circulation of skin can be activated. As a result, when the surface of face and body is rubbed with this hydroxyapatite-cleaned skin of hand, the keratin layer thereof can be easily removed, resulting in an improvement in tension of skin and in the elimination of wrinkles, thus smoothing the skin.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing a hydroxyapatite and an aqueous solution of biocompounds from tissue by electrolyzing the tissue in an aqueous solution thereby dissolving and separating tissue components in the vicinity of anode, which comprises the steps of:

(a) dissolving, in the vicinity of said anode, said tissue filled in an anode vessel of an electrolytic apparatus by passing an electric current through said tissue said electrolytic apparatus comprising;

an electrolytic bath filled with an electrolyte;

a cathode vertically disposed in said electrolyte;

said anode vessel provided on an outer wall thereof with a large number of small holes for allowing said electrolyte to flow therethrough and entirely immersed in said electrolyte; and an anode vertically disposed in said anode vessel;

(b) allowing part of said tissue components dissolved in the vicinity of said anode to crystallize in an cathode solution in the vicinity of said cathode;

(c) filtering said electrolyte to obtain a filtrate and a residue;

(d) obtaining said aqueous solution of biocompounds from said filtrate; and (e) obtaining said hydroxyapatite from said residue.

2. The method of manufacturing a hydroxyapatite and an aqueous solution of biocompounds according to claim 1, wherein said tissue is a bone of animal and/or tooth.

3. The method of manufacturing a hydroxyapatite and an aqueous solution of biocompounds according to claim 1, wherein said tissue is formed of a mixture comprising at least a bone of animal and/or tooth, and one or more kinds of tissue selected from the group consisting of meat, skin, lipid, blood and organs.

4. The method of manufacturing a hydroxyapatite and an aqueous solution of biocompounds according to claim 1, 2 or 3, wherein said hydroxyapatite contains minerals, amino acid, nucleoside, collagen and protein, and said aqueous solution of biocompounds contains minerals, amino acid, nucleoside, collagen, protein and saccharides.

5. The method of manufacturing a hydroxyapatite and an aqueous solution of biocompounds according to claim 1, 2 or 3, wherein a liquid level of said electrolytic cell is constituted by an aqueous cathode solution.

6. A method of manufacturing an aqueous solution of biocompounds by electrolyzing a tissue in an aqueous solution thereby dissolving tissue components in the vicinity of an electrode, which comprises the steps of:

(a) dissolving a tissue consisting a mixture comprising one or more kinds selected from meat, skin, lipid, blood and organs and filled in an anode vessel of an electrolytic apparatus by passing an electric current through said tissue, said electrolytic apparatus comprising;

an electrolytic bath filled with an electrolyte;

a cathode vertically disposed in said electrolyte;

said anode vessel provided on an outer wall thereof with a large number of small holes for allowing said electrolyte to flow therethrough and entirely immersed in said electrolyte; and an anode vertically disposed in said anode vessel;

(b) filtering said electrolyte to obtain a filtrate; and (c) obtaining said aqueous solution of biocompounds from said filtrate.

7. The method of manufacturing a hydroxyapatite and an aqueous solution of biocompounds according to claim 6, wherein said aqueous solution of biocompounds contains minerals, amino acid, nucleoside, collagen, protein and saccharides.

8. The method of manufacturing a hydroxyapatite and an aqueous solution of biocompounds according to claim 6 or 7, wherein a liquid level of said electrolytic cell is constituted by an aqueous cathode solution.

* * * * *

UNITED STATES PATENT AND TRADEMARK OFFICE
CERTIFICATE OF CORRECTION

PATENT NO.    : 6,149,796
DATED         : November 21, 2000
INVENTOR(S)   : H. Yamazaki et al.

It is certified that error appears in the above-identified patent and that said Letters Patent is hereby corrected as shown below:

Title Page:

Item [73],
Assignee "Chiba," should read -- Chiba-shi, --

Item [75],
Inventors: "Chiba," should read -- Chiba-shi, --
Assignee: "Hiraki" should read -- Hiraku --

Attorney, Agent, or Firm: "Jophson" should read -- Johnson --

Signed and Sealed this

Twenty-first Day of August, 2001

Attest:

NICHOLAS P. GODICI
*Attesting Officer*       *Acting Director of the United States Patent and Trademark Office*